United States Patent [19]

Lajoie et al.

[11] Patent Number: 5,236,723
[45] Date of Patent: Aug. 17, 1993

[54] PRODUCTION OF DIETARY FATTY ACID SALT PRODUCTS

[75] Inventors: M. Stephen Lajoie, Basking Ridge; Kenneth R. Cummings, Skillman, both of N.J.; Thomas F. Sweeney, Morrisville, Pa.; Alfredo Vinci, Dayton, N.J.

[73] Assignee: Church & Dwight Co., Inc., Princeton, N.J.

[21] Appl. No.: 802,264

[22] Filed: Dec. 4, 1991

[51] Int. Cl.$^5$ ................................................ A23K 1/00
[52] U.S. Cl. ........................................ 426/72; 426/74; 426/601; 426/648; 426/656; 426/658; 426/807; 514/558
[58] Field of Search .................. 426/74, 648, 72, 601, 426/656, 658, 807, 648; 514/558; 554/156, 157

[56] References Cited

U.S. PATENT DOCUMENTS

| | | | |
|---|---|---|---|
| 4,533,557 | 8/1985 | Maruyama | 426/656 |
| 4,729,896 | 3/1988 | Sawhill | 426/74 |
| 4,826,694 | 5/1989 | McAskie | 426/807 |

Primary Examiner—R. B. Penland
Attorney, Agent, or Firm—Charles B. Barris

[57] ABSTRACT

This invention provides an improved process for the production of fatty acid metal salts. An essential feature of the process is the use of a combination of basic alkaline earth metal and alkali metal compounds as salt-forming reagents.

A product of the invention process is a fatty acid salt dietary supplement composition which contains one or more additional biologically active nutrient or medicament ingredients.

21 Claims, No Drawings

PRODUCTION OF DIETARY FATTY ACID SALT PRODUCTS

CROSS-REFERENCE TO RELATED APPLICATION

The subject matter of the present patent application is related to that disclosed in patent application Ser. No. 761,235, filed Sep. 17, 1991.

BACKGROUND OF THE INVENTION

Conventional cattle feeds such as corn and alfalfa often fail to provide sufficient energy for cattle, especially lactating dairy cattle during periods of heavy milk production. Feed containing a high proportion of corn also has a tendency to depress the milk fat content of the milk produced by such cattle. Fat is a concentrated energy source, and it is known that if the proportion of fat in cattle feed is increased, lactating dairy cattle produce high milk yields without draining their reserves of body fat and without diminishing the proportion of milk fat in the milk produced.

However, it has been found that if the proportion of fat in the diet of cattle exceeds about 5% of the total feed solids, the feed has toxic effects upon the microorganisms in the rumen of the cattle. It appears that fat reduces the growth rate or even kills certain microorganisms which digest fiber in the cow's rumen, thereby lowering fiber digestibility. This deleterious effect on the cow's rumen is particularly true of unsaturated fats. Although the decreased fiber digestion in the rumen is partially compensated by greater fiber digestion in the lower parts of the alimentary canal, the total energy derived is less than that resulting from more complete microbial digestion in the rumen.

There has been a continuing need for new dietary supplements for animal feed which can be fed to ruminant animals without interfering with the rumen microorganisms, or being rendered ineffective by the rumen microorganisms.

U.S. Pat. Nos. 4,642,317; 4,826,694; 4,853,233; and 4,909,138 describe the incorporation of insoluble fatty acid salts in ruminant feed as a means of increasing the fat content of the feed without deleteriously affecting the ruminant digestion cycle. A feed additive such as fatty acid calcium salt functions as a rumen inert product which passes through the rumen without interfering with rumen fermentation (i.e., a rumen bypass product), and is subsequently metabolized in the abomasum or small intestine of the ruminant.

Accordingly, it is an object of this invention to provide a fatty acid salt composition which can function as a rumen bypass animal feed supplement, and permit a beneficial increase in the dietary fat content of the feed.

It is another object of this invention to provide an improved process for production of a fatty acid alkaline earth metal salt, utilizing a combination of basic compounds as a salt-forming reactant.

It is a further object of this invention to provide a process for production of a fatty acid salt dietary supplement composition which contains one or more additional biologically active nutrient or medicament ingredients which have rumen bypass protection.

Other objects and advantages of the present invention shall become apparent from the accompanying description and examples.

DESCRIPTION OF THE INVENTION

One or more objects of the present invention are accomplished by the provision of a process for the preparation of a dietary fatty acid salt product which comprises (1) forming an admixture of reactive ingredients comprising (a) at least one $C_{14}-C_{22}$ fatty acid, (b) between about 0.8–1.2 equivalents of basic alkaline earth metal compound per equivalent of $C_{14}-C_{22}$ fatty acid, (c) a quantity of basic alkali metal compound which provides an alkaline earth metal:alkali metal atomic ratio between about 2:1 and 20:1, (d) between about 10–50 weight percent of an aqueous medium, based on the weight of fatty acid, and (e) a biologically active ingredient; and (2) recovering the salt product after completion of the exothermic salt-forming reaction.

In another embodiment this invention provides a dietary fatty acid salt product in friable solid form which comprises (a) at least one $C_{14}-C_{22}$ fatty acid salt of an alkaline earth metal; (b) a basic alkali metal compound, wherein the atomic ratio of alkaline earth metal:alkali metal is between about 2:1 and 20:1, and (c) a biologically active ingredient.

The $C_{14}-C_{22}$ fatty acid component of the salt-forming reaction medium consists of one or more saturated or unsaturated carboxylic acids such as those derived from beef and mutton tallow, lard, cottonseed oil, palm oil, and the like.

Palm fatty acid distillate is a commercial product produced by distilling the fatty acids present in natural palm oil. A distillate product typically has the following weight percent content:

| Free fatty acids | 60–90 |
|---|---|
| Water | <1 |
| Triglycerides | 10–40 |
| Unsaponifiables | <3 |

The iodine value is less than 54 and the melting point is about 45° C. The content of peroxides is below 10 milliequivalents of oxygen per kilogram. The fatty acids in the free fatty acids and the triglycerides consist of the following weight percent:

| Palmitic acid | 38–50 |
|---|---|
| Oleic acid | 35–40 |
| Linoleic acid | 5–10 |
| Stearic acid | 3–6 |
| Lauric acid | 1–3 |

Beef tallow acids are available commercially as a byproduct obtained by alkaline extraction of waste beef fat and subsequent acidification, and normally contain the following weight percent of fatty constituents:

| Free fatty acids | 60–90 |
|---|---|
| Triglycerides | 10–40 |
| Water | <1 |
| Unsaponifiables | <3 |

The iodine value is less than 50 and the melting point is 40°–45° C. The content of peroxides is less than 10 milliequivalents of oxygen per kilogram. The fatty acids in the free fatty acids and in the triglycerides have the following weight percent content:

| | |
|---|---|
| Palmitic acid | 22–28 |
| Oleic acid | 38–44 |
| Linoleic acid | 3–6 |
| Stearic acid | 18–24 |

Because $C_{14}$–$C_{22}$ fatty acids and glycerides are susceptible to atmospheric oxidation, it is advantageous to incorporate an oil-soluble antioxidant, and a chelating agent to bind any ferric, copper, zinc or other metal capable of catalyzing atmospheric oxidation. Suitable quantities for inclusion in the fatty acid bulk are about 0.03–0.1% or higher of antioxidant as permitted by regulation, and about 0.05–0.3% of chelating agent, based on the weight of fatty acid.

Illustrative of preferred additives are butylated hydroxytoluene antioxidant and citric acid chelating agent. The chelating agent is added in an edible solvent such as propylene glycol to facilitate blending into the fatty acid.

The alkaline earth metal ingredient of the process is at least one member selected from the group consisting of basic calcium and magnesium compounds, such as oxides, carbonates, phosphates, hydroxides, and the like. The alkaline earth metal component preferably has a particle size which passes a 100 mesh U.S. standard screen.

The alkali metal ingredient is at least one member selected from the group consisting of basic sodium and potassium and lithium oxides, carbonates, bicarbonates, phosphates, hydroxides, and the like.

The biologically active ingredient of the invention process can be selected from a broad variety of nutrients and medicaments, either as a single component or as a mixture of components, which are illustrated by the following listing of active molecular species:

1. $C_2$–$C_{22}$ aliphatic carboxylic acids and esters, and alkali metal, ammonium and alkaline earth metal salts which are different than the selected $C_{14}$–$C_{22}$ fatty acid ingredient of the process.
2. sugars and complex carbohydrates which include both water-soluble and water-insoluble monosaccharides, disaccharides and polysaccharides.

Cane molasses is a byproduct from the extraction of sucrose from sugar cane. It is commercially available at standard 79.5° Brix concentration, which has a water content of about 21 weight percent, and a sugar content of 50 weight percent. Sugar beet byproducts also are available as low cost carbohydrate sources.

Whey is a byproduct of the dairy industry. The whey is a dilute solution of lactalbumin, lactose, fats, and the soluble inorganics from milk. Dried whey solids typically have the following composition:

| | |
|---|---|
| Protein | 12.0% |
| Fat | 0.7% |
| Lactose | 60.0% |
| Phosphorus | 0.79% |
| Calcium | 0.87% |
| Ash | 9.7% |

Another source of carbohydrate is derived from the pulp and paper industry which produces large quantities of byproduct lignin sulfonates from wood during the sulfite pulping process. The byproduct is recovered in the form of salts such as ammonium, sodium and magnesium lignin sulfonates.

3. aminoacid ingredients either singly or in combination which include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cysteine ethyl HCl, and the like, and analogs thereof.

4. vitamin ingredients either singly or in combination which include thiamine HCl, riboflavin, pyridoxine HCl, niacin, inositol, choline chloride, calcium pantothenate, biotin, folic acid, ascorbic acid, vitamin $B_{12}$, p-aminobenzoic acid, vitamin A acetate, vitamin K, vitamin D, vitamin E, and the like.

Trace element ingredients include compounds of cobalt, copper, manganese, iron, zinc, tin, nickel, chromium, molybdenum, iodine, chlorine, silicon, vanadium, selenium, calcium, magnesium, sodium and potassium.

5. Protein ingredients are obtained from sources such as dried blood or meat meal, cottonseed meal, soy meal, dehydrated alfalfa, dried and sterilized animal and poultry manure, fish meal, liquid or powdered egg, fish solubles, cell cream, rape seed oil (canola oil), and the like.

Protein equivalent ingredients include non-protein nitrogen compounds such as urea, biuret, ammonium phosphate, and the like.

6. medicament ingredients either singly or in combination which include promazine hydrochloride, chloromadionate acetate, chlorotetracycline, sulfamethazine, monensin, sodium monensin, poloxaline, and the like. Oxytetracycline is a preferred antibiotic for cattle prophylaxis.

7. enzymes such as lipolytic proteins which aid feed digestibility, e.g., by hydrolysis of fatty acid glycerides to free fatty acid and glycerol.

The biologically active ingredient quantity employed in the process typically will vary in the range between about 0.05–20 weight percent, based on the weight of $C_{14}$–$C_{22}$ fatty acid ingredient.

The invention process can be conducted in a batch reactor or as a continuous operation. The fatty acid, alkaline earth metal compound, alkali metal compound, biologically active ingredient and aqueous medium can be admixed simultaneously, or the fatty acid and alkaline earth metal compound can be blended first and then combined with the alkali metal compound, biologically active ingredient and aqueous medium. Alternatively, the alkaline earth metal and alkali earth metal compounds can be premixed, or the alkali metal compound can be pre-dissolved in the aqueous medium before the admixing of process ingredients.

In one processing method the fatty acid is heated to 80°–110° C., and then mixed with the basic alkaline earth metal ingredient. After the aqueous medium, basic alkali metal compound and biologically active ingredient are added to the mixture, there is a short induction period which is followed by an exothermic salt-forming reaction.

The amount of aqueous medium employed is sufficient to support the salt-forming reaction, and preferably is vaporized as steam during the exothermic reaction period to yield a friable fatty acid salt product which in granule form is suitable for use as an animal feed supplement.

The biologically active ingredient can be premixed with the $C_{14}$–$C_{22}$ fatty acid, or with the aqueous medium, as determined by the fat-solubility or water-solubility of the biologically active ingredient.

If the biologically active ingredient is sensitive to the alkaline earth metal compound hydration and salt-forming exothermic conditions at the initial reaction stage of the process, the biologically active ingredient can be added at a later reaction stage while the reaction mixture is still in a fluid state.

The use of a combination of alkaline earth metal and alkali metal compounds as the salt-forming reagent imparts several important advantages to the invention process.

As described in U.S. Pat. No. 4,826,694, the production of a fatty acid calcium or magnesium salt typically involves the use of about 50–80 percent excess of expensive calcium or magnesium basic reagent over the calculated stoichiometric quantity to insure an acceptable degree of fatty acid salt formation. In contradistinction, the basic alkaline earth metal compound in the present invention process is employed in a quantity between about 0.8–1.2 equivalents per equivalent of fatty acid, rather than a large stoichiometric excess.

Another advantage of the invention process is in the efficiency of insoluble fatty acid alkaline earth metal salt formation. It appears that the alkali metal compound present in the aqueous reaction medium interacts readily with the fatty acid component to form an intermediate fatty acid alkali metal salt. Subsequently the fatty acid alkali metal salt interacts with the hydrated alkaline earth metal compound to produce the insoluble fatty acid alkaline earth metal salt product. If the alkali metal content is in an atomic ratio between about 1:5 and 1:2 of alkali metal:alkaline earth metal, the kinetically favorable alkali metal salt intermediate reaction converts essentially all of the fatty acid from free acid to alkali metal salt. Without the presence of the basic alkali metal ions, the kinetically less favorable reaction of alkaline earth metal ions with fatty acid tends to be incomplete and some residual unreacted fatty acid remains under the processing conditions. The presence of alkali metal ions facilitates the conversion of fatty acid via the alkali metal salt intermediate to its alkaline earth metal salt derivative.

A present invention fatty acid salt product is adapted to function as a rumen bypass dietary supplement in ruminant feed. An important advantage of a present invention dietary supplement composition is the rumen bypass protection which extends to all the biologically active ingredients of the composition, such as aminoacids, vitamins, and the like, which normally are metabolized in the rumen.

The following Examples are further illustrative of the present invention. The components and specific ingredients are presented as being typical, and various modifications can be derived in view of the foregoing disclosure within the scope of the invention.

EXAMPLE I

This Example illustrates the continuous production of fatty acid calcium salt in accordance with the present invention.

The fatty acid component is a palm fatty acid distillate of the following composition:

| | |
|---|---|
| Lauric acid | 2.3% |
| Palmitic acid | 49.9% |
| Stearic acid | 5.4% |
| Oleic acid | 35.0% |

| -continued | |
|---|---|
| Linoleic acid | 7.4% |

The alkali metal component is introduced as an aqueous potassium carbonate solution. The concentration of the aqueous potassium carbonate solution is calculated to provide the required volume of water to the reaction medium, and provide potassium ions to satisfy a calcium:potassium atomic ratio of about 5:1.

The process is operated continuously with equipment which is essentially the same as described and illustrated with reference to FIG. 1 of U.S. Pat. No. 4,826,694 by W. McAskie.

Calcium oxide from a hopper and hot palm oil distillate (96° C.) from a supply line are mixed in predetermined proportions in a mixing pump. The aqueous potassium carbonate solution is added to the reactant admixture via a supply line.

A sidestream of the aqueous potassium carbonate solution is withdrawn upstream from the salt-forming reaction zone. The sidestream is utilized as a solvent to form a solution of methionine hydroxy analog potassium salt. The sidestream solution is blended back into the main aqueous potassium carbonate stream before it enters the salt-forming reaction zone.

The combined aqueous medium streams are supplied to the reaction zone at a rate which provides about 30 weight percent of water, and 2 weight percent of methionine hydroxy analog potassium salt, based on the weight of palm fatty acid distillate.

The hydrated mixture formed in the process is passed through a mixing pump and the resultant semi-liquid reaction medium at about 100° C. is discharged as a spread layer onto a continuously moving conveyor belt. Steam evolves from the conveyor transported reaction mass.

At the end of the conveyor belt solid lumps of reaction product fall through a sizing machine onto a second conveyor belt. In this conveying zone the salt-forming reaction and evolution of water proceed to completion. The essentially dry fatty acid calcium salt product is passed through a sifter, and collected in bags suitable for transportation and storage.

The residence time on the first conveyor is about 30 minutes, and the overall production time from reactant mixing to collection of the dry granulated product is about 2.5 hours.

The final product has a total fatty acid calcium salt content of 85 weight percent, a methionine hydroxy analog content of 1.5 weight percent, a water content of about 3–5 weight percent, and an ash content of about 15 weight percent.

The invention fatty acid calcium salt product can be incorporated as a dietary supplement in cattle feed such as hay silage or corn silage, in a calculated quantity which will provide each animal about 100 grams per day of fatty acid salt, and about 1.4 grams per day of methionine hydroxy analog.

The process is repeated, except that 3 weight percent of methionine as the biologically active ingredient is premixed with the palm fatty acid distillate, prior to admixture with the other process ingredients.

EXAMPLE II

This Example illustrates the preparation of a dietary fatty acid calcium salt product which contains vitamin A and trace minerals.

Calcium oxide (100 g), sodium carbonate (15 g) and palm fatty acid distillate (700 g) are admixed, and then the mixture is blended with an aqueous suspension medium (300 g) with stirring. Steam evolves during the exothermic salt-forming reaction, and the final product is in the form of a friable solid.

The aqueous suspension medium starting material employed in the process is prepared with the following ingredients:

| | |
|---|---|
| Soy bean meal | 300 g |
| Soy lecithin | 10 g |
| Tricalcium phosphate | 5 g |
| Trace minerals[1] | 2 g |
| Vitamin A | 1 g |

The listed ingredients are blended to form a homogeneous dry mixture. The dry mixture is added to one liter of water with high speed stirring to form an aqueous suspension medium.

| | Weight Ratio |
|---|---|
| [1]$CoSO_4.7H_2O$ | 4 |
| $CuSO_4.5H_2O$ | 5 |
| $MnSO_4.H_2O$ | 6 |
| $FeSO_4.7H_2O$ | 7 |
| $ZnSO_4.H_2O$ | 3 |

What is claimed is:

1. A process for the preparation of a dietary fatty acid salt product which comprises (1) forming an admixture of reactive ingredients consisting essentially of (a) at least one $C_{14}$–$C_{22}$ fatty acid, (b) between about 0.8–1.2 equivalents of basic alkaline earth metal compound per equivalent of $C_{14}$–$C_{22}$ fatty acid, (c) a quantity of basic alkali metal compound which provides an alkaline earth metal:alkali metal atomic ratio between about 2:1 and 20:1, (d) between about 10–50 weight percent of an aqueous medium, based on the weight of fatty acid, and (e) between about 0.05–20 weight percent of a biologically active ingredient, based on the weight of $C_{14}$–$C_{22}$ fatty acid; and (2) recovering an salt product after completion of the exothermic salt-forming reaction; wherein the salt product is substantially free of unreacted $C_{14}$–$C_{22}$ fatty acid and wherein the presence of alkali metal ions facilitates conversion of fatty acid via an alkali metal salt intermediate to its alkaline earth metal salt.

2. A process in accordance with claim 1 wherein the fatty acid ingredient is a mixture comprising 0–10 percent lauric acid, 0–60 percent palmitic acid, 0–10 percent stearic acid, 0–60 percent oleic acid, and 0–10 percent linoleic acid.

3. A process in accordance with claim 1 wherein the alkaline earth metal ingredient is a basic calcium compound or magnesium compound or a mixture thereof.

4. A process in accordance with claim 1 wherein the alkali metal ingredient is a basic sodium compound or potassium compound or a mixture thereof.

5. A process in accordance with claim 1 wherein the $C_{14}$–$C_{22}$ fatty acid and alkaline earth metal compound are premixed before admixture with the other process ingredients.

6. A process in accordance with claim 1 wherein the alkaline earth metal compound and alkali metal compound are premixed before admixture with the other process ingredients.

7. A process in accordance with claim 1 wherein the alkali metal compound and aqueous medium are premixed before admixture with the other process ingredients.

8. A process in accordance with claim 1 wherein the biologically active ingredient and aqueous solution are premixed before admixture with the other process ingredients.

9. A process in accordance with claim 1 wherein the biologically active ingredient and $C_{14}$–$C_{22}$ fatty acid are premixed before admixture with the other process ingredients.

10. A process in accordance with claim 1 wherein the biologically active ingredient is added after the other ingredients have been admixed and the salt-forming reaction has commenced.

11. A process in accordance with claim 1 wherein the biologically active ingredient is a nutrient.

12. A process in accordance with claim 1 wherein the biologically active ingredient is a medicament.

13. A process in accordance with claim 1 wherein the biologically active ingredient comprises at least one aminoacid.

14. A process in accordance with claim 1 wherein the biologically active ingredient comprises at least one polypeptide.

15. A process in accordance with claim 1 wherein the biologically active ingredient comprises at least one antibiotic.

16. A process in accordance with claim 1 wherein the biologically active ingredient comprises at least one water-soluble or water-insoluble carbohydrate.

17. A process in accordance with claim 1 wherein the biologically active ingredient comprises at least one vitamin or trace element.

18. A process in accordance with claim 1 wherein the salt-forming reaction medium is at a temperature between about 60°–110° C.

19. A process in accordance with claim 1 wherein water evaporation occurs during the salt-forming reaction, and the salt product is recovered in the form of friable granules.

20. A dietary fatty acid salt product in friable solid form which consists essentially of (a) at least one $C_{14}$–$C_{22}$ fatty acid salt of an alkaline earth metal; (b) a basic alkali metal compound, wherein the atomic ratio of alkaline earth metal:alkali metal is between about 2:1 and 20:1; and (c) between about 0.05–20 weight percent of a biologically active ingredient, based on the weight of $C_{14}$–$C_{22}$ fatty acid in the product; wherein the salt product is substantially free of unreacted $C_{14}$–$C_{22}$ fatty acid and wherein the presence of alkali metal ions facilitates conversion of fatty acid via an alkali metal salt intermediate to its alkaline earth metal salt.

21. A salt product in accordance with claim 20 wherein the alkaline earth metal is calcium and the alkali metal is sodium or potassium or a mixture thereof.

* * * * *